(12) United States Patent
Hara et al.

(10) Patent No.: US 7,935,425 B2
(45) Date of Patent: *May 3, 2011

(54) INSULATING FILM MATERIAL CONTAINING ORGANIC SILANE OR ORGANIC SILOXANE COMPOUND, METHOD FOR PRODUCING SAME, AND SEMICONDUCTOR DEVICE

(75) Inventors: Daiji Hara, Kanagawa (JP); Keisuke Yoshida, Yamaguchi (JP)

(73) Assignee: Tosoh Corporation, Yamaguchi-ken (JP)

( * ) Notice: Subject to any disclaimer, the term of this patent is extended or adjusted under 35 U.S.C. 154(b) by 887 days.

This patent is subject to a terminal disclaimer.

(21) Appl. No.: 10/536,352

(22) PCT Filed: Nov. 28, 2003

(86) PCT No.: PCT/JP03/15281
§ 371 (c)(1),
(2), (4) Date: Dec. 14, 2005

(87) PCT Pub. No.: WO2004/049422
PCT Pub. Date: Jun. 10, 2004

(65) Prior Publication Data
US 2006/0151884 A1 Jul. 13, 2006

(30) Foreign Application Priority Data

Nov. 28, 2002 (JP) ................................. 2002346226
Jul. 17, 2003 (JP) ................................. 2003198654

(51) Int. Cl.
*B32B 9/04* (2006.01)
*C23C 16/40* (2006.01)
(52) U.S. Cl. .................. 428/446; 427/225.18; 427/387; 556/460; 556/462
(58) Field of Classification Search .......................... None
See application file for complete search history.

(56) References Cited

U.S. PATENT DOCUMENTS

| | | | |
|---|---|---|---|
| 3,763,212 A | 10/1973 | McEntee et al. | |
| 5,120,680 A | 6/1992 | Foo et al. | |
| 5,594,079 A * | 1/1997 | Hara et al. | 526/119 |
| 5,852,153 A * | 12/1998 | Sugo et al. | 528/14 |
| 6,030,706 A | 2/2000 | Eissa et al. | |
| 6,887,578 B2 * | 5/2005 | Gleason et al. | 428/447 |
| 7,011,890 B2 * | 3/2006 | Nguyen et al. | 428/447 |
| 7,288,292 B2 * | 10/2007 | Gates et al. | 427/489 |
| 7,413,775 B2 * | 8/2008 | Hara et al. | 427/249.15 |
| 2002/0127412 A1 * | 9/2002 | Leman et al. | 428/447 |
| 2002/0142579 A1 | 10/2002 | Vincent et al. | |
| 2002/0192980 A1 | 12/2002 | Hogle et al. | |
| 2004/0253777 A1 | 12/2004 | Miyoshi et al. | |
| 2005/0070730 A1 * | 3/2005 | Bannou et al. | 556/465 |
| 2005/0267253 A1 | 12/2005 | Hayashi | |
| 2007/0093078 A1 * | 4/2007 | Harada et al. | 438/790 |
| 2008/0274627 A1 * | 11/2008 | Hamada et al. | 438/787 |

FOREIGN PATENT DOCUMENTS

| | | |
|---|---|---|
| DE | 33 04 822 C1 | 6/1984 |
| EP | 118 625 * | 9/1984 |
| EP | 826791 A2 | 3/1998 |
| GB | 1 014 156 A | 12/1965 |
| JP | 2-192729 A | 7/1990 |
| JP | 05-279856 | 10/1993 |
| JP | 6-345781 A | 12/1994 |
| JP | 7-115091 A | 5/1995 |

(Continued)

OTHER PUBLICATIONS

Abstract of EP 118 625.*

(Continued)

*Primary Examiner* — Marc S Zimmer
(74) *Attorney, Agent, or Firm* — Sughrue Mion, PLLC

(57) ABSTRACT

A material for insulating film suitable as an interlayer insulating material for a semiconductor device, from which an insulating film is formed by chemical vapor deposition, and an insulating film formed from such a material and a semiconductor device employing an insulating film, are provided. A material for insulating film comprising an organosilicon compound which is one of an organosilane compound in which a secondary hydrocarbon group and an alkenyl group, or an alkenyl group, is directly bonded to a silicon atom, or an organosiloxane compound in which a secondary hydrocarbon group and/or an alkenyl group is directly bonded to a silicon atom, represented by the formulae (1) to (4), from which an insulating film is formed by chemical vapor deposition of the organosilicon compound:

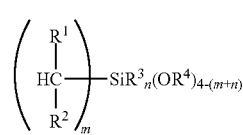

(1)

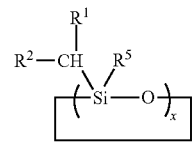

(2)

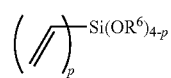

(3)

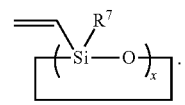

(4)

16 Claims, No Drawings

FOREIGN PATENT DOCUMENTS

| | | | |
|---|---|---|---|
| JP | 07-115091 A | 5/1995 | |
| JP | 7-273194 A | 10/1995 | |
| JP | 9-223693 A | 8/1997 | |
| JP | 09-223693 A | 8/1997 | |
| JP | 9 227685 A | 9/1997 | |
| JP | 10-144670 | 5/1998 | |
| JP | 10-284486 | 10/1998 | |
| JP | 11-288931 | 10/1999 | |
| JP | 2000-302791 | 10/2000 | |
| JP | 2001-274153 A | 10/2001 | |
| JP | 2002-110670 | 4/2002 | |
| JP | 2002-179687 A | 6/2002 | |
| JP | 2002-201416 A | 7/2002 | |
| JP | 2002-256434 A | 9/2002 | |
| JP | 2003-45870 A | 2/2003 | |
| JP | 2004-47873 A | 2/2004 | |
| WO | WO 03/019645 A1 | 3/2003 | |
| WO | WO 03/040156 | * | 5/2003 |

OTHER PUBLICATIONS

Tamao, Kohei, et al., Silafunctional compounds in organic synthesis. 22. Some new aspects of conjugate addition of Grignard and alkyl-lithium reagents to vinylsilanes: Tetrahedron Letters, 25 (18), 1905-8 Coden: Teleay; ISSN 0040-4039, 1984, XP002463556.

Tanaka, T. Heats of formation of lower members of dimethyl- and methylisopropoxy-cyclopolysiloxanes, Journal of the Chemical Society of Japan, vol. 33, No. 3, 1960, pp. 282-286.

Arnason, I.: "13C NMR Investigation of Si-alkylsubstituted 1, 3, 5-trisilacyclohexanes", Z. Anorg. Allg.Chem, vol. 624, 1998, pp. 1973-1976.

Goikhman, R. et al: "Transition metal-catalyzed silanone generation", Journal of the American Chemical Society, vol. 118, 1996, pp. 10894-10895.

Extended European Search Report dated Feb. 1, 2011 issued in corresponding application No. 10191051.1.

* cited by examiner

INSULATING FILM MATERIAL CONTAINING ORGANIC SILANE OR ORGANIC SILOXANE COMPOUND, METHOD FOR PRODUCING SAME, AND SEMICONDUCTOR DEVICE

TECHNICAL FIELD

The present invention relates to a low dielectric constant interlayer insulating film material used in multilayer interconnect technology in logic ULSI. Particularly, it relates to a material for insulating film composed of either organosilicon compound of an organosilane compound and an organosiloxane compound for plasma polymerization, and its use.

BACKGROUND ART

In the production technology in the field of integrated circuit in an electronics industry, demand for high integration and high speed has been increasing. With respect to silicon ULSI, particularly logic ULSI, performance of the wiring which connects MOSFET, rather than the performance of MOSFET itself by its miniaturization has been problematic. Namely, in order to solve the problem of wiring delay due to multilayer interconnect, reduction of wiring resistance and reduction of capacity between wirings and between layers have been required.

Accordingly, at present, introduction of copper wiring having a lower electric resistance and having a migration resistance, instead of aluminum wiring used for the most part of the integrated circuit, is essential, and a process comprising seed formation by sputtering or chemical vapor deposition (hereinafter referred to simply as CVD) method, followed by copper plating, has been used practically.

As the low dielectric constant interlayer insulating film material, various ones have been proposed. Heretofore, as the inorganic system, silicon dioxide ($SiO_2$), silicon nitride and phosphosilicate glass, and as the organic system, polyimides have been employed. In recent years, with a purpose of obtaining a more homogeneous interlayer insulating film, it has been proposed that a tetraethoxysilane monomer is preliminarily hydrolyzed, i.e., subjected to polycondensation to obtain $SiO_2$, which is used as a coating material called "spin on glass" (inorganic SOG), and it has been proposed to use a polysiloxane obtained by polycondensation of an organoalkoxysilane monomer as organic SOG.

Further, as a method of forming the insulating film, there are two methods including a coating method comprising coating an insulating film polymer solution by e.g. spin coating to carry out film formation and a CVD method comprising plasma polymerization mainly in a plasma CVD equipment to carry out film formation.

As the plasma CVD method, for example, JP-A-2002-110670 proposes a method of forming an oxidized trimethylsilane thin film from trimethylsilane and oxygen by the plasma CVD method. Further, JP-A-11-288931 proposes a method of forming an oxidized alkylsilane thin film from an alkoxysilane having a straight chain alkyl group such as methyl, ethyl or n-propyl, an alkynyl group such as vinyl phenyl and an aryl group, by the plasma CVD method. An insulating film formed by such conventional plasma CVD material has favorable adhesion properties to a barrier metal and a copper wiring material which is a wiring material, on the contrary, uniformity of the film may be problematic, or the film deposition rate or the dielectric constant may be insufficient in some cases.

On the other hand, the film formed by the coating method has favorable uniformity, however, three steps of coating, solvent removal and heat treatment are required, such being economically disadvantageous as compared with a film formed by the CVD method. Further, adhesion properties to a barrier metal and a copper wiring material which is a wiring material, and uniform coating itself of the coating liquid to a miniaturized substrate structure tend to be problematic in many cases.

Further, with respect to the materials in the coating method, a method of making materials be porous has been proposed so as to achieve an ultra low-k material having a dielectric constant of at most 2.5, more preferably at most 2.0. A method of dispersing organic component fine particles which are easily pyrolyzed into an organic or inorganic material matrix, followed by heat treatment to make the material be porous, and a method of depositing $SiO_2$ ultrafine particles formed by evaporation of silicon and oxygen in a gas, to form a thin film of $SiO_2$ ultrafine particles, may, for example, be mentioned.

However, although these methods of making the material be porous, are effective to achieve a low dielectric constant, mechanical strength tends to decrease, whereby chemical mechanical polishing (CMP) may be difficult, or increase of the dielectric constant and wiring corrosion due to absorption of moisture may be caused in some cases.

Accordingly, the market further requires a well-balanced material which satisfies all the requirements such as a low dielectric constant, an adequate mechanical strength, adhesion properties to a barrier metal, prevention of copper dispersion, plasma ashing resistance and moisture absorption resistance. In order to satisfy these requirements to a certain extent, an organosilane type material having an increased proportion of carbon in the organic substituent to silane, thereby having characteristics intermediate between the organic polymer and the inorganic polymer has been proposed.

For example, JP-A-2000-302791 proposes a method to obtain an interlayer insulating film not being porous and having a dielectric constant of at most 2.4, by using a coating solution obtained by hydrolysis and polycondensation of a silicon compound having an adamantyl group by a sol-gel method in the presence of an aqueous acid solution.

However, this material is a material for the coating method, and there are still problems of the above-described film formation method by the film coating method.

DISCLOSURE OF THE INVENTION

Under these circumstances, the present invention has been made to solve the above problems, and it is an object of the present invention to provide a novel low dielectric constant material, particularly a material for a low dielectric constant insulating film, containing either organosilicon compound of an organosilane compound and an organosiloxane compound, suitable for a PECVD equipment, and to provide an insulating film employing it, and a semiconductor device containing such an insulating film.

The present inventors have found that either organosilicon compound of an organosilane compound and an organosiloxane compound having such a structure that a secondary hydrocarbon group and/or an alkenyl group is directly bonded to a silicon atom, is suitable as a material for an insulating film, particularly a low dielectric constant interlayer insulating film for a semiconductor device, and accomplished the present invention.

Namely, the present invention resides in a material for insulating film comprising an organosilicon compound of one of the following formulae (1) to (4), from which an insulating film is formed by chemical vapor deposition of the organosilicon compound:

an organosilane compound represented by the following formula (1) having such a structure that a secondary hydrocarbon group and an alkenyl group are directly bonded to a silicon atom:

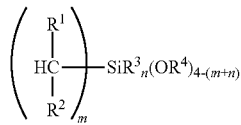
formula (1)

wherein each of $R^1$ and $R^2$ represents a $C_{1-20}$ hydrocarbon group, $R^3$ represents a $C_{1-20}$ hydrocarbon group having at least one alkenyl group, or an alkenyl group and an aryl group, $R^4$ represents a $C_{1-10}$ hydrocarbon group or a hydrogen atom, m represents an integer of from 1 to 2, n represents an integer of from 1 to 2, and m+n represents an integer of from 2 to 3;

an organosiloxane compound represented by the following formula (2) having such a structure that a secondary hydrocarbon group and/or an alkenyl group is directly bonded to a silicon atom:

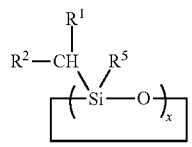
formula (2)

wherein $R^1$ and $R^2$ are as defined above, $R^5$ represents a $C_{1-20}$ hydrocarbon group or a hydrogen atom, and x represents an integer of 2 or above;

an organosilane compound represented by the following formula (3) having such a structure that a vinyl group is directly bonded to a silicon atom:

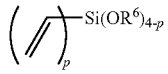
formula (3)

wherein $R^6$ represents a $C_{1-10}$ hydrocarbon group or a hydrogen atom, and p represents 2 or 3;

an organosiloxane compound represented by the following formula (4) having such a structure that a vinyl group is directly bonded to a silicon atom:

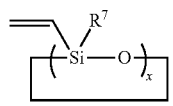
formula (4)

wherein $R^7$ represents one of a $C_{1-20}$ alkyl group, an alkenyl group and an aryl group, and x is as defined above.

BEST MODE FOR CARRYING OUT THE INVENTION

Now, the present invention will be explained in detail below.

In the above formula (1), each of $R^1$ and $R^2$ is a $C_{1-20}$ saturated or unsaturated hydrocarbon group, and may have any of straight chain, branched chain and cyclic structures. Further, a structure that groups bond to each other is included in the present invention. If the carbon number exceeds 20, it tends to be difficult to obtain a material such as a corresponding organic halide, or even if it can be obtained, the purity tends to be low in some cases.

Taking stable use in a CVD equipment into consideration, a $C_{1-10}$ hydrocarbon group is particularly preferred from such a viewpoint that the vapor pressure of the organosilane compound will not be too low.

Examples of the hydrocarbon group for each of $R^1$ and $R^2$ are not particularly limited, and a $C_{1-20}$, preferably $C_{1-10}$, alkyl group, an aryl group, an arylalkyl group and an alkylaryl group may be mentioned. $R^1$ and $R^2$ may be the same or different.

As examples of a case where $R^1$ and $R^2$ are not bonded to each other, a secondary hydrocarbon group may be mentioned wherein $R^1$ and $R^2$ are at least one member or at least two members selected from the group consisting of methyl, ethyl, n-propyl, isopropyl, n-butyl, i-butyl, sec-butyl, tert-butyl, n-pentyl, tert-amyl, n-hexyl, cyclohexyl, phenyl and toluyl groups.

As examples of a secondary hydrocarbon group in a group in which $R^1$ and $R^2$ are bonded to each other and bonded to Si by means of secondary carbon, cyclobutyl, cyclobutenyl, cyclopentyl, cyclopentadienyl, cyclohexyl, cyclohexenyl, cyclooctenyl and cyclooctadienyl groups may be mentioned as typical examples.

As the combination of $R^1$ and $R^2$, an iso-propyl group wherein $R^1$ and $R^2$ are both methyl, a sec-butyl group wherein $R^1$ and $R^2$ are methyl and ethyl, and cyclopentyl, cyclopentadienyl, cyclohexyl and cyclohexenyl groups wherein $R^1$ and $R^2$ are bonded to each other, are preferred from an economical viewpoint.

$R^3$ is a $C_{1-20}$ hydrocarbon group having at least one alkenyl group, or an alkenyl group and an aryl group. As the alkenyl group, vinyl, 1-propenyl, 1-butenyl, 1-pentenyl, 1-hexenyl, 2-propenyl, 2-butenyl, 2-pentenyl and 2-hexenyl may be mentioned as typical examples. Particularly, the alkenyl group is preferably a vinyl group. Further, as the hydrocarbon group other than the alkenyl group, a $C_{1-20}$ hydrocarbon group other than an aryl group, such as the same group as $R^1$ and $R^2$ may be mentioned.

$R^4$ represents a $C_{1-10}$ hydrocarbon group or a hydrogen atom, and the hydrocarbon group may be a saturated or unsaturated hydrocarbon group, and may have any of straight chain, branched chain and cyclic structures. If the carbon number exceeds 10, the vapor pressure of the formed organosilane tends to be low and its use in a PECVD equipment may be difficult in some cases, such being unfavorable.

$R^4$ is preferably methyl, ethyl, n-propyl, isopropyl, n-butyl, i-butyl, sec-butyl or tert-butyl which is a $C_{1-4}$ hydrocarbon group in view of preparation of the material.

m represents an integer of from 1 to 2, n represents an integer of from 1 to 3, and m+n represents an integer of 3 or under. Namely, a hydrocarbon group wherein m=1 and n=1 or m=2 and n=0 represents a disubstituted dialkoxysilane, and a hydrocarbon group wherein m=1 and n=2, m=2 and n=1, or m=3 and n=0 represents a trisubstituted alkoxysilane. A mixture thereof is included in the present invention.

Specific examples of the organosilane compound represented by the above formula (1) include:

(A) isopropylvinyldimethoxysilane, isopropylvinyldiethoxysilane, isopropylvinyl-di-tert-butoxysilane, diisopropylvinylmethoxysilane, diisopropylvinylethoxysilane, diisopropylvinyl-tert-butoxysilane, isopropyldivinylmethoxysilane, isopropyldivinylethoxysilane, isopropyldivinyl-tert-butoxysilane, isopropylvinylmethylmethoxysilane, isopropylvinylmethylethoxysilane, isopropylvinylmethyl-tert-butoxysilane, isopropylvinylethylmethoxysilane, isopropylvinylethylethoxysilane, isopropylvinylethyl-tert-butoxysilane, sec-butylvinyldimethoxysilane, sec-butylvinyldiethoxysilane, sec-butylvinyl-di-tert-butoxysilane, di-sec-butylvinylmethoxysilane, di-sec-butylvinylethoxysilane, di-sec-butylvinyl-tert-butoxysilane, sec-butyldivinylmethoxysilane, sec-butyldivinylethoxysilane and sec-butyldivinyl-tert-butoxysilane.

In the above formula (2), each of $R^1$ and $R^2$ may be the same one as in the above formula (1). $R^5$ represents a $C_{1-20}$ hydrocarbon group or a hydrogen atom, and the hydrocarbon group may, for example, be the same one as defined for each of $R^1$, $R^2$ and $R^3$.

Specific examples of the organosiloxane compound represented by the above formula (2) include (B) 1,3,5-triisopropyl-1,3,5-trivinylcyclotrisiloxane, 1,3,5,7-tetraisopropyl-1,3,5,7-tetravinylcyclotetrasiloxane, 1,3,5,7,9-pentaisopropyl-1,3,5,7,9-pentavinylcyclopentasiloxane, 1,3,5-tri-sec-butyl-1,3,5-trivinylcyclotrisiloxane, 1,3,5,7-tetra-sec-butyl-1,3,5,7-tetravinylcyclotetrasiloxane and 1,3,5,7,9-penta-sec-butyl-1,3,5,7,9-pentavinylcyclopentasiloxane, (C) 1,3,5-triisopropyl-1,3,5-trimethylcyclotrisiloxane, 1,3,5,7-tetraisopropyl-1,3,5,7-tetramethylcyclotetrasiloxane, 1,3,5,7,9-pentaisopropyl-1,3,5,7,9-pentamethylcyclopentasiloxane, 1,3,5-triisopropyl-1,3,5-triethylcyclotrisiloxane, 1,3,5,7-tetraisopropyl-1,3,5,7-tetraethylcyclotetrasiloxane, 1,3,5,7,9-pentaisopropyl-1,3,5,7,9-pentaethylcyclopentasiloxane, hexaisopropylcyclotrisiloxane, octaisopropylcyclotetrasiloxane, decaisopropylcyclopentasiloxane, 1,3,5-tri-sec-butyl-1,3,5-trimethylcyclotrisiloxane, 1,3,5,7-tetra-sec-butyl-1,3,5,7-tetramethylcyclotetrasiloxane, 1,3,5,7,9-penta-sec-butyl-1,3,5,7,9-pentamethylcyclopentasiloxane, 1,3,5-tri-sec-butyl-1,3,5-triethylcyclotrisiloxane, 1,3,5,7-tetra-sec-butyl-1,3,5,7-tetraethylcyclotetrasiloxane and 1,3,5,7,9-penta-sec-butyl-1,3,5,7,9-pentaethylcyclopentasiloxane, (D) 1,3,5-triisopropylcyclotrisiloxane, 1,3,5,7-tetraisopropylcyclotetrasiloxane, 1,3,5,7,9-pentaisopropylcyclopentasiloxane, 1,3,5-tri-sec-butylcyclotrisiloxane, 1,3,5,7-tetra-sec-butylcyclotetrasiloxane and 1,3,5,7,9-penta-sec-butylcyclopentasiloxane.

In the above formula (3), $R^6$ represents a $C_{1-10}$ hydrocarbon group or a hydrogen atom, and the hydrocarbon group may be the same one as defined for $R^4$.

Specific examples of the organosilane compound represented by the above formula (3) having such a structure that a vinyl group is directly bonded to a silicon atom, include (E) divinyldimethoxysilane, divinyldiethoxysilane, divinyl di-tert-butoxysilane, trivinylmethoxysilane, trivinylethoxysilane and trivinyl tert-butoxysilane.

In the above formula (4), $R^7$ represents a $C_{1-20}$ alkyl group, an alkenyl group or an aryl group, specifically, methyl, ethyl, vinyl, n-propyl, iso-butyl or the like may be mentioned.

Specific examples of the organosiloxane compound represented by the above formula (4) having such a structure that a vinyl group is directly bonded to a silicon atom, include (F) 1,3,5-trimethyl-1,3,5-trivinylcyclotrisiloxane, 1,3,5,7-tetramethyl-1,3,5,7-tetravinylcyclotetrasiloxane, 1,3,5,7,9-pentamethyl-1,3,5,7,9-pentavinylcyclopentasiloxane, 1,3,5-triethyl-1,3,5-trivinylcyclotrisiloxane, 1,3,5,7-tetraethyl-1,3, 5,7-tetravinylcyclotetrasiloxane and 1,3,5,7,9-pentaethyl-1,3,5,7,9-pentavinylcyclopentasiloxane, (G) hexavinylcyclotrisiloxane, octavinylcyclotetrasiloxane and decavinylcyclopentasiloxane.

The method for producing the organosilane compound of the above formula (1) is not particularly limited. For example, the organosilane compound represented by the formula (1) can be produced by reacting an organic compound represented by the following formula (5):

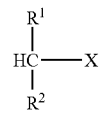

formula (5)

wherein $R^1$ and $R^2$ are as defined above, and X represents a hydrogen atom, a chlorine atom, a bromine atom or an iodine atom, with organolithium or metal lithium granule to produce a compound in which a secondary hydrocarbon group and a lithium atom are directly bonded, and reacting this compound with a halogenated organosilane or a halogenated organoalkoxysilane represented by the following formula (6):

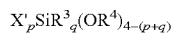

formula (6)

wherein X' represents a fluorine atom, a chlorine atom, a bromine atom or an iodine atom, $R^3$ and $R^4$ are as defined above, p represents an integer of from 0 to 4, q represents an integer of from 1 to 2, and p+q represents an integer of 4 or under.

Further, the organosilane compound represented by the formula (1) can be produced by using metal magnesium instead of the organolithium or the metal lithium granule in the above production method.

Examples of the organic compound represented by the formula (5) wherein X is a chlorine atom, a bromine atom or an iodine atom include isopropyl chloride, isopropyl bromide, isopropyl iodide, sec-butyl chloride, sec-butyl bromide, sec-butyl iodide, cyclopentyl chloride, cyclopentyl bromide, cyclopentyl iodide, cyclohexyl chloride, cyclohexyl bromide and cyclohexyl iodide.

Further, examples of the organic compound represented by the formula (5) wherein X is a hydrogen atom include cyclopentadiene, pentamethylcyclopentadiene and 1,2,3,4-tetramethyl-1,3-cyclopentadiene. By reacting organolithium such as n-butyl lithium or tert-butyl lithium with such a compound, a compound in which a secondary hydrocarbon group and a lithium atom are directly bonded, can be produced.

Examples of the halogenated organosilane, halogenated organoalkoxysilane or tetraalkoxysilane represented by the formula (6) include vinyltriethoxysilane, vinyltrimethoxysilane, divinyldimethoxysilane, divinyldiethoxysilane, vinylmethyldimethoxysilane, vinylethyldimethoxysilane, vinyl n-propyldimethoxysilane, vinyl n-butyldimethoxysilane, vinylmethyldimethoxysilane, vinylethyldimethoxysilane, vinyl n-propyldimethoxysilane, vinyl n-butyldimethoxysilane, vinyltrichlorosilane, divinyldichlorosilane, vinylmethyldichlorosilane, vinylethyldichlorosilane, vinylmethyldichlorosilane, vinylethyldichlorosilane, vinyl n-propyldichlorosilane, vinyl n-butyldichlorosilane, phenylvinyldichlorosilane, phenylvinyldimethoxysilane and phenylvinyldiethoxysilane, each having at least one alkenyl group.

Further, after the preparation reaction, when a halogen atom directly bonded to silicon remains in the alkoxysilane substituted by a hydrocarbon group as a product, an alkali metal alkoxide represented by the following formula (7) is reacted therewith for alkoxylation:

R⁴OM  formula (7)

wherein M is an alkali metal, and R⁴ is as defined above.

Examples of the alkali metal alkoxide represented by the formula (7) include lithium methoxide, lithium ethoxide, lithium-i-propoxide, sodium methoxide, sodium ethoxide, sodium-i-propoxide, potassium methoxide, potassium ethoxide, potassium-i-propoxide and potassium-tert-butoxide.

By employing the present production method, the organosilane compound represented by the formula (1) with a high purity can be obtained with a high yield while suppressing formation of by-products.

The conditions for production of the compound in which a secondary hydrocarbon group and a lithium atom are directly bonded, are not particularly limited, and one example is shown below.

As the metal lithium to be used, a lithium wire, a lithium ribbon or a lithium shot may, for example, be employed, and it is preferred to employ lithium fine particles having a particle size of at most 500 μm in view of reaction efficiency.

As the metal magnesium to be used, a magnesium ribbon, magnesium granule or a magnesium powder may, for example, be employed.

As the organolithium to be used, a n-hexane solution of n-butyl lithium or a n-pentane solution of tert-butyl lithium may, for example, be employed.

The solvent to be used for the reaction is not particularly limited so long as it is used for said technical field. For example, a saturated hydrocarbon such as n-pentane, i-pentane, n-hexane, cyclohexane, n-heptane or n-decane, an unsaturated hydrocarbon such as toluene, xylene or decene-1, or an ether such as diethyl ether, dipropyl ether, tert-butyl methyl ether, dibutyl ether or cyclopentyl methyl ether, may be used. Further, a mixed solvent thereof may also be used.

The reaction temperature for the above reaction is preferably such a temperature range that the formed compound in which a secondary carbon atom and a lithium atom are bonded, or compound in which a secondary hydrocarbon group and a magnesium atom are directly bonded, will not decompose. The reaction is preferably carried out usually at a temperature of from −100 to 200° C. which is industrially employed, preferably at a temperature of from −85 to 150° C. As the pressure condition of the reaction, the reaction may be carried out under elevated pressure, normal pressure or reduced pressure.

The prepared compound in which a secondary hydrocarbon group and a lithium atom are directly bonded or compound in which a secondary hydrocarbon group and a magnesium atom are directly bonded, may be used as it is after the production, or it may be used after unreacted organic halide, metal lithium or metal magnesium, and lithium halide or magnesium halide as a reaction by product are removed.

The conditions of the reaction of the compound in which a secondary hydrocarbon group and a lithium atom are directly bonded or compound in which a secondary hydrocarbon group and a magnesium atom are directly bonded thus obtained, and the halogenated organosilane or the halogenated organoalkoxysilane of the above formula (6), are not particularly limited, and one example is shown below.

As the reaction solvent to be used, the same solvents as the solvents which can be used for the production of the above compound in which a secondary hydrocarbon group and a lithium atom (or a magnesium atom) are directly bonded may be used. The reaction temperature is preferably such a temperature range that the compound in which a secondary hydrocarbon group and/or an alkenyl group and a lithium atom (or a magnesium atom) are directly bonded, will not decompose. The reaction is preferably carried out usually at a temperature of from −100 to 200° C. which is industrially employed, preferably at a temperature of from −85 to 150° C. As the pressure condition of the reaction, the reaction may be carried out under elevated pressure, normal pressure or reduced pressure.

The method for producing the organosiloxane compound of the above formula (2) is not particularly limited, and it can be produced, for example, by reacting a halogenated alkoxysilane compound substituted by a secondary hydrocarbon group, represented by the following formula (8) having such a structure that a secondary hydrocarbon group is directly bonded to a silicon atom, with water in the presence of an acid or a base:

formula (8)

wherein R¹, R², R⁴, R⁵ and X are as defined above, and s represents an integer of from 0 to 2. For example, the dialkoxysilane substituted by a secondary hydrocarbon group of the above (A) as an example of the organosilane compound represented by the above formula (1), or a compound having an alkoxy group of the above compound substituted by chlorine, bromine, iodine or fluorine may be used.

One having an alkoxy group of the above compound substituted by chlorine, bromine, iodine or fluorine can be obtained by changing the conditions in the same method for producing the compound of the above formula (1). Further, the compound of the above formula (8) thus obtained may contain the compound of the above formula (1) or (3).

As the acid which coexist at the time of reaction, an inorganic acid such as hydrochloric acid, nitric acid or sulfuric acid, or an organic acid such as toluenesulfonic acid may be employed.

The reaction solvent to be used for production of the organosiloxane compound represented by the formula (2) is not particularly limited so long as it is used for said technical field. For example, a saturated hydrocarbon such as n-pentane, i-pentane, n-hexane, cyclohexane, n-heptane or n-decane, an unsaturated hydrocarbon such as toluene, xylene or decene-1, an ether such as diethyl ether, dipropyl ether, tert-butyl methyl ether, dibutyl ether, cyclopentyl methyl ether or tetrahydrofuran, or an alcohol such as methanol, ethanol, isopropanol, n-butanol, tert-butanol or 2-ethylhexanol may be employed. Further, a mixed solvent thereof may also be employed. Particularly when an ether or an alcohol is employed, an organosiloxane compound of the formula (2) having a specific molecular weight can be produced with a high yield in some cases.

As the reaction temperature for production of the organosiloxane compound represented by the formula (2), the reaction is preferably carried out usually at a temperature of from −100 to 200° C. which is industrially employed, preferably at a temperature of from −85 to 150° C. As the pressure condition of the reaction, the reaction may be carried out under elevated pressure, normal pressure or reduced pressure.

The method for producing the organosilane compound of the above formula (3) is not particularly limited, and it can be produced, for example, by reacting an alkoxysilane such as tetramethoxysilane or tetraethoxysilane with a vinyl organic metal compound such as vinyl lithium, vinyl magnesium chloride or vinyl magnesium chloride. Further, it can be produced also by reacting a halogenated silane such as tetrachlorosilane with a vinyl organic metal compound such as vinyl lithium, vinyl magnesium chloride or vinyl magnesium chloride, and then reacting the alkali metal alkoxide of the above formula (7) therewith. As the conditions for production, the same conditions as in the method for producing the compound of the above formula (1) may be employed.

The method for producing the organosiloxane compound of the above formula (4) is not particularly limited, and it can be produced, for example, by the same method as the method for producing the compound of the above formula (2) employing as a material a halogenated organosilane or a halogenated organoalkoxysilane having at least one alkenyl group represented by the above formula (6).

When the produced organosilane compound or organosiloxane compound represented by one of the formulae (1) to (4) is used as an insulating film material, it is preferred that the moisture content is less than 50 ppm and that the content of impurity elements other than silicon, carbon, oxygen and hydrogen, derived from reactant materials, is less than 10 ppb. Accordingly, it is preferred to purify such an organosilicon compound by means of filtration using e.g. a glass filter or a sintered porous body, distillation under normal pressure or under reduced pressure, or column separation using silica, alumina or a polymer gel, to remove lithium salts or magnesium salts as by products. In such a case, as the case requires, the above purification means may be used in combination. By a method of extracting lithium salts or magnesium salts as by-products with e.g. water, which is employed for general organic synthesis technology, the moisture content and the content of impurity elements other than silicon, carbon, oxygen and hydrogen, particularly the content of metal impurity residue, in the organosilane compound or the organosiloxane compound represented by one of the formulae (1) to (4) to be finally obtained, tend to be high, and such a compound is inappropriate as a material for insulating film in some cases.

Further, in a case where a by-product containing a silanol structure is formed, hydroxyl groups of the silanol are treated with e.g. sodium hydride or potassium hydride so that the by-product is precipitated in a form of a sodium salt or a potassium salt, and then the alkoxysilane substituted by a hydrocarbon group as the main product can be isolated by distillation.

For production, the operation is in accordance with a method in the field of said organometal compound synthesis. Namely, it is preferred that the reaction is carried out in an atmosphere of dehydrated and deoxidized nitrogen or argon, and a solvent, a column packing material for purification, etc., to be used are preliminarily subjected to dehydration operation. Further, it is preferred that impurities such as metal residue and particles are removed.

The organosilane compounds and the organosiloxane compounds represented by the formulae (1) to (4) of the present invention are materials suitable as a material for low dielectric constant insulating film formation by a PECVD equipment.

The method for forming the insulating film material of the present invention is not particularly limited. A PECVD equipment which is commonly used in the field of said technology such as a semiconductor production field or a liquid crystal display production field, is used to form an insulating film. The PECVD equipment means an equipment in which a material for insulating film such as an organosilane is vaporized by a vaporizer and introduced to the inside of a film formation chamber, and a voltage is applied to an electrode in the film formation chamber by a high frequency power source to generate plasma, to form a plasma polymerization film on e.g. a silicon substrate in the film formation chamber. At this time, for the purpose of generating plasma, a gas such as argon or helium or an oxidizing agent such as oxygen or nitrous oxide may be introduced. When film formation is carried out by a PECVD equipment using the material of the present invention for insulating film, a thin film suitable as a low dielectric constant material (low-k material) for a semiconductor device can be formed.

Formation of an insulating film under PECVD conditions under which the cyclic siloxane structure of the organosiloxane compound of the above formula (2) or (4) is maintained is included in the present invention. The insulating film obtained by the present method is a porous insulating film of a cyclic organosiloxane compound, most of the pores of which have small pore sizes of 1 nm or under, and is a thin film particularly suitable as a low dielectric constant material (low-k material) for a semiconductor device having low dielectric characteristics and having high mechanical properties and high heat transmission properties. As the PECVD conditions in such a case, it is preferred to carry out PECVD film formation with a relatively low plasma power (W, voltage×current) as shown in Examples for example, so as not to destroy the cyclic siloxane structure. Specifically, it is carried out preferably under from 1 W to 2,000 W, preferably from 1 W to 1,000 W. Further, an insulating film having lower dielectric characteristics can be formed at a high film formation rate by using a cyclic organosiloxane in which a vinyl group and an isopropyl group are bonded to the same silicon atom.

A porous low dielectric constant insulating film can be obtained also by forming one of the materials of the formulae (1) to (4) into a film by CVD, and then subjecting the film to a heat treatment at a temperature of 350 deg. ° C. or over at which bond between one of the secondary hydrocarbon group, the alkenyl group, the alkyl group and the aryl group and the silicon atom is broken. The heat treatment temperature is preferably 350 deg. ° C. or over at which formation into a porous body is completed, and 500 deg. ° C. or under at which a semiconductor device will not deteriorate.

The low dielectric-constant material of the present invention is suitable for production of ULSI employing multilayer interconnect, and a semiconductor device employing it is also included in the present invention.

Now, the present invention will be explained in detail with reference to Examples. However, the present invention is by no means restricted to such specific Examples.

Example 1

Preparation of Organomagnesium in which a Secondary Hydrocarbon Group and a Magnesium Atom are Directly Bonded 53.4 g (2.20 mol) of metal magnesium and 1.60 L of dry diethyl ether were charged in a 2 L four-necked flask equipped with a dropping funnel and a mechanical stirrer in a stream of nitrogen, and cooled to 0° C. A solution having 246 g (2.00 mol) of isopropyl bromide diluted with 200 ml of dry diethyl ether was dropwise added thereto with stirring over a period of 100 minutes, and reaction was carried out at room temperature for 14 hours to obtain a diethyl ether solution of isopropyl magnesium bromide.

Preparation of Organosilane Compound Having Such a Structure that a Secondary Hydrocarbon Group and a Vinyl Group are Directly Bonded to a Silicon Atom 206 g (1.39 mol) of vinyl trimethoxysilane and 300 ml of dry diethyl ether were charged in a 2 L four-necked flask equipped with a dropping funnel and a mechanical stirrer in a stream of nitrogen, and cooled to 0° C. 1.67 mol of the above prepared diethyl ether solution of isopropyl magnesium bromide was dropwise added thereto with stirring over a period of 120 minutes, and reaction was carried out at room temperature for 2 hours. After completion of the reaction, magnesium methoxide residue as a by-product was removed by filtration, and the obtained filtrate was distilled under reduced pressure to obtain 141 g (0.882 mol) of isopropylvinyldimethoxysilane as an aimed product. The yield was 63.5%.

The isolated isopropylvinyldimethoxysilane was analyzed by $^1$H-NMR, $^{13}$C-NMR and GC-MS, and the results were as follows.

$^1$H-NMR: δ1.07 ppm (s, 6H, 2CH$_3$), δ1.08 ppm (s, 1H, CH), δ3.62 ppm (s, 6H, 2OCH$_3$), δ5.95-6.30 ppm (m, 3H, CH=CH$_2$)

$^{13}$C-NMR: δ12.0 ppm, 16.7 ppm, 50.7 ppm, δ130.2 ppm, δ136.4 ppm

GC-MS: Mw=160, C$_7$H$_{16}$O$_2$Si

Further, the moisture and magnesium contents in 100 g of the obtained isopropylvinyldimethoxysilane were measured by means of a Karl Fischer moisture meter and ICP-MS (inductively coupled plasma mass spectrometer, manufactured by Yokogawa Analytical Systems, Inc., tradename "HP4500") and as a result, H$_2$O=5 ppm and Mg<10 ppb, and the obtained product was useful as a material for insulating film.

Example 2

Preparation of Organosilane Compound Having Such a Structure that Two Vinyl Groups are Directly Bonded to a Silicon Atom 306 g (2.00 mol) of divinyldichlorosilane, 539 g (4.80 mol) of potassium tert-butoxide and 3.0 L of dry hexane were charged in a 5 L four-necked flask equipped with a dropping funnel and a mechanical stirrer in a stream of nitrogen, and reaction was carried out for 17 hours under reflux with hexane. After completion of the reaction, potassium chloride residue as a by-product was removed by filtration, and the obtained filtrate was distilled under reduced pressure to obtain 257 g (1.13 mol) of divinyl di-tert-butoxysilane as an aimed product. The yield was 56.5%.

The isolated divinyl di-tert-butoxysilane was analyzed by $^1$H-NMR and GC-MS, and the results were as follows.

$^1$H-NMR: δ1.39 ppm (s, 18H, 2$^t$BuO), δ5.87-6.28 ppm (m, 6H, 2CH=CH$_2$)

GC-MS: Mw=228, C$_{12}$H$_{24}$O$_2$Si

Further, the moisture and potassium contents in 100 g of the obtained divinyl di-tert-butoxysilane were measured by means of a Karl Fischer moisture meter and ICP-MS (inductively coupled plasma mass spectrometer, manufactured by Yokogawa Analytical Systems, Inc., tradename "HP4500") and as a result, H$_2$O=4 ppm and K<10 ppb, and the obtained product was useful as a material for insulating film.

Example 3

Preparation of Organosiloxane Compound Having Such a Structure that a Secondary Hydrocarbon Group and a Vinyl Group are Directly Bonded to a Silicon Atom 500 g (3.09 mol) of isopropylvinyldimethoxysilane, 556 g (30.9 mol) of pure water, 152 g (1.55 mol) of sulfuric acid and 3.00 L of tetrahydrofuran were charged in a 5 L four-necked flask equipped with a mechanical stirrer, and reaction was carried out for 1 hour under reflux. After completion of the reaction, THF and water were distilled off, and the obtained organic layer was dried by molecular sieves. After drying, 255 g (0.746 mol) of 1,3,5-triisopropyl-1,3,5-trivinylcyclotrisiloxane as an aimed product was obtained from the organic layer by distillation under reduced pressure. The yield was 24.1%, and the conversion ratio of isopropylvinyldimethoxysilane was 72.4%.

The isolated 1,3,5-triisopropyl-1,3,5-trivinylcyclotrisiloxane was analyzed by $^1$H-NMR and GC-MS, and the results were as follows.

$^1$H-NMR: δ1.05-1.14 (m, 21H, $^i$Pr), δ5.88-6.23 ppm (m, 9H, CH=CH$_2$)

$^{13}$C-NMR: δ14.4 ppm, δ14.5 ppm, δ16.3 ppm, δ133.1 ppm, δ133.2 ppm, δ133.4 ppm, δ134.6 ppm, δ134.8 ppm, δ135.0 ppm GC-MS: Mw=342, C$_{15}$H$_{30}$O$_3$Si$_3$ Further, moisture and magnesium contents in 100 g of the obtained 1,3,5-triisopropyl-1,3,5-trivinylcyclotrisiloxane were measured by means of a Karl Fischer moisture meter and ICP-MS (inductively coupled plasma mass spectrometer, manufactured by Yokogawa Analytical Systems, Inc., tradename "HP4500") and as a result, H$_2$O=8 ppm and Mg<10 ppb, and the obtained product was useful as a material for insulating film.

Example 4

In the same manner as in Example 6 except that 458 g (3.09 mol) of isopropylmethyldimethoxysilane was used instead of 500 g (3.09 mol) of isopropylvinyldimethoxysilane in Example 3, 1,3,5-triisopropyl-1,3,5-trimethylcyclotrisiloxane was produced. The yield was 25.3%, and the conversion ratio of isopropylmethyldimethoxysilane was 75.8%.

The isolated 1,3,5-triisopropyl-1,3,5-trimethylcyclotrisiloxane was analyzed by $^1$H-NMR, $^{13}$C-NMR and GC-MS, and the results were as follows.

$^1$H-NMR: δ0.197-0.213 ppm (m, 9H, CH$_3$), δ1.06-1.10 (m, 21H, $^i$Pr), $^{13}$C-NMR: δ15.3 ppm, δ15.5 ppm, δ16.4 ppm, δ16.5 ppm GC-MS: Mw=306, C$_{12}$H$_{30}$O$_3$Si$_3$ Further, moisture and magnesium contents in 100 g of the obtained 1,3,5-triisopropyl-1,3,5-trimethylcyclotrisiloxane were measured by means of a Karl Fischer moisture meter and ICP-MS (inductively coupled plasma mass spectrometer, manufactured by Yokogawa Analytical Systems, Inc., tradename "HP4500") and as a result, H$_2$O=9 ppm and Mg<10 ppb, and the obtained product was useful as a material for insulating film.

Example 5

Preparation of Organosiloxane Compound Having Such a Structure that a Vinyl Group is Directly Bonded to a Silicon Atom 1,250 g (69.4 mol) of pure water and 1,250 g (16.9 mol) of tert-butanol were charged in a 5 L four-necked flask equipped with a dropping funnel and a mechanical stirrer in a stream of nitrogen, 500 g (3.27 mol) of divinyldichlorosilane was dropwise added thereto from the dropping funnel at room temperature over a period of 1 hour, and reaction was carried out further for 1 hour. After completion of the reaction, octavinylcyclotetrasiloxane as an aimed product was extracted with 1.0 L of n-pentane, and the obtained n-pentane layer was dried by molecular sieves. After drying, 144 g (0.368 mol) of octavinylcyclotetrasiloxane as an aimed product was obtained from the pentane layer by distillation under reduced pressure. The yield was 11.3%, and the conversion ratio of divinyldichlorosilane was 45.0%.

The isolated octavinylcyclotetrasiloxane was analyzed by $^1$H-NMR and GC-MS, and the results were as follows.

$^1$H-NMR: δ5.90-6.32 ppm (m, CH=CH$_2$)
GC-MS: Mw=392, C$_{16}$H$_{24}$O$_4$Si$_4$ Further, moisture and magnesium contents in 100 g of the obtained octavinylcyclotetrasiloxane were measured by means of a Karl Fischer moisture meter and ICP-MS (inductively coupled plasma mass spectrometer, manufactured by Yokogawa Analytical Systems, Inc., tradename "HP4500") and as a result, H$_2$O=9 ppm and Mg<10 ppb, and the obtained product was useful as a material for insulating film.

Example 6

Preparation of Organosiloxane Compound Having Such a Structure that a Vinyl Group and an Alkyl Group are Directly Bonded to a Silicon Atom In the same manner as in Example 5 except that 500 g (3.55 mol) of vinylmethyldichlorosilane was used instead of 500 g (3.27 mol) of divinyldichlorosilane in Example 5, 1,3,5,7-tetravinyl-1,3,5,7-tetramethylcyclotetrasiloxane was produced. The yield was 16.5%, and the conversion ratio of vinylmethyldichlorosilane was 66.0%.

The isolated 1,3,5,7-tetravinyl-1,3,5,7-tetramethylcyclotetrasiloxane was analyzed by $^1$H-NMR and GC-MS, and the results were as follows.

$^1$H-NMR: δ0.255-0.290 ppm (m, 12H, CH$_3$) δ5.90-6.32 ppm (m, 12H, CH=CH$_2$)
GC-MS: Mw=344, C$_{12}$H$_{24}$O$_4$Si$_4$ Further, moisture and magnesium contents in 100 g of the obtained 1,3,5,7-tetravinyl-1,3,5,7-tetramethylcyclotetrasiloxane were measured by means of a Karl Fischer moisture meter and ICP-MS (inductively coupled plasma mass spectrometer, manufactured by Yokogawa Analytical Systems, Inc., tradename "HP4500") and as a result, H$_2$O=9 ppm and Mg<10 ppb, and the obtained product was useful as a material for insulating film.

Example 7

Plasma Polymerization

Using a plasma polymerization equipment NL-OP50FT manufactured by Nippon Laser Electronics Co., divinyl di-tert-butoxysilane was subjected to plasma polymerization under a discharge voltage of 2.1 kV at a discharge current of 5.0 mA under a divinyl di-tert-butoxysilane partial pressure of 0.7 torr at room temperature for a polymerization (discharge) time of 12 minutes, and a film thereof was formed on a silicon substrate. The results are shown below.

Film formation rate: 46.7 nm/min.
Thin film composition (XPS)
C=41.3 at %, O=36.7 at %, Si=22.0 at %,
C/Si=1.88 atomic ratio,
O/Si=1.67 atomic ratio
Observation of thin film cross section by SEM:
Flat dense film
The film was a thin film having a high proportion of carbon (organic substituent) relative to silicon, suitable as a material for insulating film.

Comparative Example 1

Film formation by plasma polymerization was carried out on a silicon substrate in the same manner as in Example 7 except that dimethyldimethoxysilane was used as the monomer to be polymerized. The results are shown below.

Film formation rate: 10.8 nm/min.
Thin film composition (XPS)
C=32.2 at %, O=40.6 at %, Si=27.1 at %
C/Si=1.19 atomic ratio,
O/Si=1.50 atomic ratio
Observation of thin film cross section by SEM:
Flat dense film
The film formation rate was low and the proportion of carbon (organic substituent) relative to silicon was low as compared with Example 7, and only a thin film unsuitable as a material for insulating film was obtained.

Example 8

Plasma Polymerization

Film formation by plasma polymerization was carried out on a silicon substrate in the same manner as in Example 7 except that isopropylvinyldimethoxysilane was used as the monomer to be polymerized. The results are shown below.

Film formation rate: 100 nm/min.
Thin film composition (XPS)
C=56.6 at %, O=25.1 at %, Si=18.3 at %
C/Si=3.09 atomic ratio,
O/Si=1.37 atomic ratio
Observation of thin film cross section by SEM:
Flat dense film
The obtained film was a thin film having a high proportion of carbon (organic substituent) relative to silicon, suitable as a material for insulating film.

Example 9

Plasma Polymerization

Film formation by plasma polymerization was carried out on a silicon substrate in the same manner as in Example 7 except that 1,3,5,7-tetravinyl-1,3,5,7-tetramethylcyclotetrasiloxane was used as the monomer to be polymerized. The results are shown below.

Film formation rate: 153 nm/min.
Thin film composition (XPS)
C=58.7 at %, O=20.9 at %, Si=20.4 at %
C/Si=2.88 atomic ratio,
O/Si=1.02 atomic ratio
Observation of thin film cross section by SEM:
Flat dense film
The obtained film was a thin film having a high proportion of carbon (organic substituent) relative to silicon, suitable as a material for insulating film. Further, the O/Si=1.00 atomic ratio in the monomer was maintained, and it is suggested that the monomer cyclic structure was maintained.

Example 10

Plasma Polymerization

Film formation by plasma polymerization was carried out on a silicon substrate in the same manner as in Example 7 except that 1,3,5-triisopropyl-1,3,5-trivinylcyclotrisiloxane was used as the monomer to be polymerized. The results are shown below.

Film formation rate: 215 nm/min.
Thin film composition (XPS)
C=68.5 at %, O=15.8 at %, Si=15.7 at %
C/Si=4.36 atomic ratio,
O/Si=1.01 atomic ratio
Observation of thin film cross section by SEM:
Flat dense film The obtained film was a thin film having a higher proportion of carbon (organic substituent) relative to silicon than Example 9, suitable as a material for insulating film. Further, the O/Si=1.00 atomic ratio in the monomer was maintained, and it is suggested that the monomer cyclic structure was maintained.

Example 11

Plasma Polymerization

Film formation by plasma polymerization was carried out on a silicon substrate in the same manner as in Example 7 except that 1,3,5-triisopropyl-1,3,5-trimethylcyclotrisiloxane was used as the monomer to be polymerized. The results are shown below.

Film formation rate: 117 nm/min
Thin film composition (XPS)
C=60.8 at %, O=20.1 at %, Si=19.1 at %
C/Si=3.18 atomic ratio,
O/Si=1.05 atomic ratio
Observation of thin film cross section by SEM:
Flat dense film The obtained film was a thin film having a higher proportion of carbon (organic substituent) relative to silicon than Example 9, suitable as a material for insulating film. Further, the O/Si=1.00 atomic ratio in the monomer was maintained, and it is suggested that the monomer cyclic structure was maintained.

INDUSTRIAL APPLICABILITY

According to the present invention, the following remarkable effects will be obtained. Namely, as the first effect of the present invention, a material having a low dielectric constant and high mechanical strength can be provided as a low dielectric constant material for an interlayer insulating film of a semiconductor device, by using an organosilane compound and/or an organosiloxane compound having such a structure that a secondary hydrocarbon group and/or an alkenyl group is directly bonded to a silicon atom of the present invention. Further, according to the present invention, an organosilane compound and/or an organosiloxane compound having such a structure that a secondary hydrocarbon group and/or an alkenyl group is directly bonded to a silicon atom, useful as a material for interlayer insulating film by a PECVD method, can be efficiently produced with high purity.

The invention claimed is:

1. A method for producing the organosilane compound represented by the formula (2):

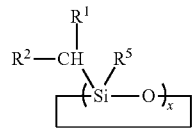

formula (2)

wherein
x represents an integer of 3 or above,
each of $R^1$ and $R^2$ represents a $C_{1-20}$ hydrocarbon group,
$R^5$ represents a $C_{1-20}$ hydrocarbon group or a hydrogen atom, which comprises reacting a halogenated alkoxysilane compound substituted by a secondary hydrocarbon group, represented by the following formula (8) having such a structure that a secondary hydrocarbon group is directly bonded to a silicon atom:

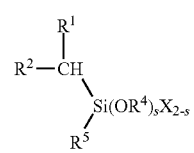

formula (8)

wherein $R^1$, $R^2$, $R^5$ are as defined above,
$R^4$ represents a $C_{1-10}$ hydrocarbon group or hydrogen atom,
X represents a hydrogen atom, a chlorine atom, a bromine atom or an iodine atom; and
s represents an integer of from 0 to 2, with water in the presence of an acid or a base.

2. An insulating film formed by introducing at least one compound selected from the group consisting of compounds of formulae (1), (2) and (4) in a PECVD equipment followed by film formation with plasma:

an organosilane compound represented by the formula (1) having such a structure that a secondary hydrocarbon group and an alkenyl group are directly bonded to a silicon atom:

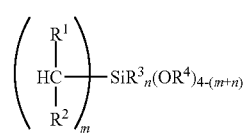

formula (1)

wherein each of $R^1$ and $R^2$ represents a $C_{1-20}$ hydrocarbon group, $R^3$ represents a $C_{1-20}$ hydrocarbon group having at least one alkenyl group, $R^4$ represents a $C_{1-10}$ hydrocarbon group or a hydrogen atom, m and n each represent 1;

an organosiloxane compound represented by the formula (2) having such a structure that a secondary hydrocarbon group is directly bonded to a silicon atom:

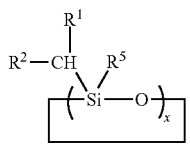
formula (2)

wherein R¹ and R² are as defined above, R⁵ represents a C$_{1-20}$ hydrocarbon group or a hydrogen atom, and x represents an integer of 3 or above, wherein two substitutents bonded to the Si in formula (2) are different;

an organosiloxane compound represented by the formula (4) having such a structure that a vinyl group is directly bonded to a silicon atom:

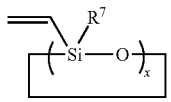
formula (4)

wherein R⁷ represents a vinyl group and x is as defined above, and, wherein, the organosiloxane compound of formula (4) is selected from the group consisting of hexavinylcyclotrisiloxane, octavinylcyclotetrasiloxane, and decavinylcyclopentasiloxane.

3. The insulating film according to claim 2, which has a cyclic siloxane structure of the organosiloxane compound of the formula (2) and/or (4).

4. The insulating film according to claim 2, which is formed into a porous body by subjecting the insulating film to a heat treatment at a temperature of at least a temperature at which bond between a silicon atom and one of a secondary hydrocarbon group, an alkyl group, an alkenyl group and an aryl group is broken.

5. A semiconductor device comprising the insulating film according to claim 2.

6. The insulating film according to claim 3, which is formed into a porous body by subjecting the insulating film to a heat treatment at a temperature of at least a temperature at which bond between a silicon atom and one of a secondary hydrocarbon group, an alkyl group, an alkenyl group and an aryl group is broken.

7. A semiconductor device comprising the insulating film according to claim 3.

8. A semiconductor device comprising the insulating film according to claim 4.

9. A material for insulating film comprising an organosilicon compound, from which an insulating film is formed by chemical vapor deposition of the ogranosilicon compound, wherein the organosilicon compound is one of 1,3,5-triisopropyl-1,3,5-trivinylcyclotrisiloxane, 1,3,5,7-tetraisopropyl-1,3,5,7-tetravinylcyclotetrasiloxane, 1,3,5,7,9-pentaisopropyl-1,3,5,7,9-pentavinylcyclopentasiloxane, 1,3,5-tri-sec-butyl-1,3,5-trivinylcyclotrisiloxane, 1,3,5,7-tetra-sec-butyl-1,3,5,7-tetravinylcyclotetrasiloxane, 1,3,5,7,9-penta-sec-butyl-1,3,5,7,9-pentavinylcyclopentasiloxane, 1,3,5-triisopropyl-1,3,5-trimethylcyclotrisiloxane, 1,3,5,7-tetraisopropyl-1,3,5,7-tetramethylcyclotetrasiloxane, 1,3,5,7,9-pentaisopropyl-1,3,5,7,9-pentamethylcyclopentasiloxane, 1,3,5-triisopropyl-1,3,5-triethylcylotrisiloxane, 1,3,5,7-tetraisopropyl-1,3,5,7-tetraethylcyclotetrasiloxane, 1,3,5,7,9-pentaisopropyl-1,3,5,7,9-pentaethylcyclopentasiloxane, 1,3,5-tri-sec-butyl-1,3,5-trimethylcyclotrisiloxane, 1,3,5,7-tetra-sec-butyl-1,3,5,7-tetramethylcyclotetrasiloxane, 1,3,5,7,9-penta-sec-butyl-1,3,5,7,9-pentamethylcyclopentasiloxane, 1,3,5-tri-sec-butyl-1,3,5-triethylcyclotrisiloxane, 1,3,5,7-tetra-sec-butyl-1,3,5,7-tetraethylcyclotetrasiloxane and 1,3,5,7,9-penta-sec-butyl-1,3,5,7,9-pentaethylcyclopentasiloxane.

10. A material comprising an organosilicon compound, wherein the compounds are represented by the following formula (2):

an organosiloxane compound represented by the formula (2) having such a structure that a secondary hydrocarbon group is directly bonded to a silicon atom:

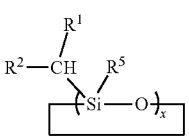
formula (2)

wherein each of R¹ and R² represents a C$_{1-20}$ hydrocarbon group, R⁵ represents a C$_{1-20}$ hydrocarbon group or a hydrogen atom, and x represents an integer of 3 or above, wherein the two substituents bonded to the Si in formula (2) are different; and are selected from the group consisting of:

a hexaalkyltricyclotrisiloxane whose two substituents bonded to the Si atom are different alkyl groups, a cyclotrisiloxane having, as a substituent, an alkenyl group or an aryl group bonded to the Si atom, and a cyclosiloxane which is a four or more Si—O unit membered ring including a cyclotetrasiloxane.

11. A method for forming an insulating film, which is formed by introducing at least one compound of the formulae (2) and (4) in a PECVD equipment, followed by film formation with plasma;

an organosiloxane compound represented by the formula (2) having such a structure that a secondary hydrocarbon group is directly bonded to a silicon atom:

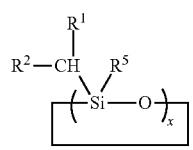
formula (2)

wherein each of R¹ and R² represents a C$_{1-20}$ hydrocarbon group, R⁵ represents a C$_{1-20}$ hydrocarbon group or a hydrogen atom, and x represents an integer of 3 or above, wherein two substitutents bonded to the Si in formula (2) are different;

an organosiloxane compound represented by the formula (4) having such a structure that a vinyl group is directly bonded to a silicon atom:

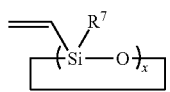

formula (4)

wherein R⁷ represents a vinyl group and x is as defined above, and, wherein, the organosiloxane compound of formula (4) is selected from the group consisting of hexavinylcyclotrisiloxane, octavinylcyclotetrasiloxane, and decavinylcyclopentasiloxane.

12. A compound selected from a group consisting of:
(i) 1,3,5-triisopropyl-1,3,5-trivinylcyclotrisiloxane, 1,3,5,7-tetraisopropyl-1,3,5,7-tetravinylcyclotetrasiloxane, 1,3,5,7,9-pentaisopropyl-1,3,5,7,9-pentavinylcyclopentasiloxane, 1,3,5-tri-sec-butyl-1,3,5-trivinylcyclotrisiloxane, 1,3,5,7-tetra-sec-butyl-1,3,5,7-tetravinylcyclotetrasiloxane, 1,3,5,7,9-penta-sec-butyl-1,3,5,7,9-pentavinylcyclopentasiloxane, 1,3,5-triisopropyl-1,3,5-trimethylcyclotrisiloxane, 1,3,5,7-tetraisopropyl-1,3,5,7-tetramethylcyclotetrasiloxane, 1,3,5,7,9-pentaisopropyl-1,3,5,7,9-pentamethylcyclopentasiloxane, 1,3,5-triisopropyl-1,3,5-triethylcyclotrisiloxane, 1,3,5,7-tetraisopropyl-1,3,5,7-tetraethylcyclotetrasiloxane, 1,3,5,7,9-pentaisopropyl-1,3,5,7,9-pentaethylcyclopentasiloxane,
(ii) 1,3,5-tri-sec-butyl-1,3,5-trimethylcyclotrisiloxane, 1,3,5,7-tetra-sec-butyl-1,3,5,7-tetramethylcyclotetrasiloxane, 1,3,5,7,9-penta-sec-butyl-1,3,5,7,9-pentamethylcyclopentasiloxane, 1,3,5-tri-sec-butyl-1,3,5-triethylcyclotrisiloxane, 1,3,5,7-tetra-sec-butyl-1,3,5,7-tetraethylcyclotetrasiloxane and 1,3,5,7,9-penta-sec-butyl-1,3,5,7,9-pentaethylcyclopentasiloxane.

13. A method for forming an insulating film which is formed by introducing the compound of formula (9) in a PECVD equipment followed by film formation with plasma,

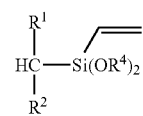

(9)

wherein R¹ and R² represents a $C_{1-20}$ hydrocarbon group, and R⁴ represents a $C_{1-10}$ hydrocarbon group or a hydrogen atom.

14. An insulating film formed by introducing the compound of the formula (9) in a PECVD equipment followed by film formation with plasma,

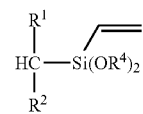

(9)

wherein R¹ and R² represents a $C_{1-20}$ hydrocarbon group, and R⁴ represents a $C_{1-10}$ hydrocarbon group or a hydrogen atom.

15. The method according to claim 13, wherein the compound of the formula (9) is isopropylvinyldimethoxysilane, isopropylvinyldiethoxysilane, isopropylvinyl-di-tert-butoxysilane, sec-butylvinyldimethoxysilane, sec-butylvinyldiethoxysilane or sec-butylvinyl-di-tert-butoxysilane.

16. The insulating film according to claim 14, wherein the compound of the formula (9) is isopropylvinyldimethoxysilane, isopropylvinyldiethoxysilane, isopropylvinyl-di-tert-butoxysilane, sec-butylvinyldimethoxysilane, sec-butylvinyldiethoxysilane or sec-butylvinyl-di-ter-butoxysilane.

* * * * *